United States Patent [19]
Cundasawmy et al.
[11] Patent Number: 4,770,794
[45] Date of Patent: Sep. 13, 1988

[54] FOAM FIRE EXTINGUISHING COMPOSITIONS FOR AERIAL FIRE EXTINGUISHING

[75] Inventors: Edward Cundasawmy, Thurso; George Cowan, Ottawa, both of Canada

[73] Assignee: Wormald Canada Inc., Mississauga, Canada

[21] Appl. No.: 882,338

[22] Filed: Jul. 7, 1986

[51] Int. Cl.[4] .......................... B01J 13/00; A62D 1/08; C09K 3/00; A61K 9/00

[52] U.S. Cl. .......................................... 252/3; 169/45; 169/46; 252/6.5; 252/8.05; 252/307; 252/602; 252/603; 252/607; 252/611

[58] Field of Search ........................ 252/3, 2, 6.5, 8.05, 252/601, 307, 602, 356, 603, 357, 607, 350, 606, 382, 610-611; 169/45, 46

[56] References Cited

U.S. PATENT DOCUMENTS

| | | | |
|---|---|---|---|
| 3,422,011 | 1/1969 | Jackovitz et al. | 252/8.05 |
| 3,553,128 | 1/1971 | Wilson | 252/8.1 |
| 3,609,074 | 9/1971 | Rainaldi et al. | 252/3 |
| 3,637,022 | 1/1972 | Kelly et al. | 252/8.05 |
| 3,984,334 | 10/1976 | Hopper | 252/8.05 |
| 4,042,522 | 8/1977 | Falk | 252/8.05 |
| 4,439,329 | 3/1984 | Kleiner et al. | 252/3 |
| 4,442,018 | 4/1984 | Rand | 252/307 |
| 4,459,221 | 7/1984 | Hisamoto et al. | 252/356 |
| 4,610,311 | 9/1986 | Bronner et al. | 252/8.05 |

OTHER PUBLICATIONS

B. Hoffman and S. Jung, "EXPYROL W 1, am neues Schaumloschmittel fur die Bekamfung von Waldbranded", ALLGEMEINE FORST ZEITSCHRIFT, vol. 36, Sep. 11, 1982, p. 1093.

J. G. Goldammer, "Die Anwendung von Schlaumloschmittein in der Waldbrandbekamfung und die Versuchergebrisse mit EXPYROL W 1", ALLGEMEINE FORST ZEITSCHRIF, vol. 36, Sep. 11, 1982, p. 1094.

*Primary Examiner*—Stephen J. Lechert, Jr.
*Assistant Examiner*—Howard J. Locker
*Attorney, Agent, or Firm*—Morgan & Finnegan

[57] ABSTRACT

Compositions and methods for retarding and extinguishing forest fires and ground fires by dropping air-activated foam compositions comprising 1% to 80% hydrocarbon surfactants, 0.1% to 6% by weight foam stabilizers, 0% to 30% by weight of solvents and 1% to 98.9% by weight of water.

16 Claims, No Drawings

FOAM FIRE EXTINGUISHING COMPOSITIONS FOR AERIAL FIRE EXTINGUISHING

BACKGROUND OF THE INVENTION

Forest fires have increased in incidence in the recent past. Most fires, until recently, were fought with water only. However, the use of water has had a limited effect upon the retardation of forest fires due to inaccessability and the relative slowness of delivering water to the fires. Often, water runs off dry ground and away from the fire area.

Fire retardant material has been dropped from airplanes or helicopters onto forest fires. Fire retardants may be classified as short-term or long-term retardants. For example, U.S. Pat. No. 3,553,128 describes a short-term fire retardant material which relies solely upon water to retard combustion. Long-term retardants contain a chemical that retards flaming combustion after the water has evaporated.

Currently, the most commonly used retardants are ammonium phosphate salts. Often, long-term retardants are thickened with additives such as polysaccharides. However, numerous problems have been encountered in using existing long-and short-term retardants. Existing retardants have a short shelf-life, cannot be easily mixed properly, decay under high-temperature conditions or cannot be used with hard water or sea water. Furthermore, although these chemicals can retard fires, they cannot extinguish them. Current retardants merely decrease the rate at which the fires spread, but cannot create a barrier to prevent the fires from spreading at all. Retardants create a "fire break" or absence of fire in their vicinity but can not provide an even fire barrier. Fires can create a path to penetrate the firebreak and continue to burn forest past the fire break point. Furthermore, the retardants could not penetrate moss and duff on the ground of the forest, which provide fuel for the fire.

Thus, the need for an effective fire retardant material which could create a long-lasting fire break was clear.

OBJECTS OF THE INVENTION

An object of this invention is to provide a composition capable of working with water to great a fire break in a forest being consumed by fire and extinguishing the fire.

Another object of this invention is to provide a fire retardant and extinguishing composition.

Yet another object of this invention is to provide a fire retardant composition which can control fires from an accessible area.

Another object of this invention is to provide a composition which will not damage vegetation or humans.

Still another object of this invention is to provide a non-corrosive fire retardant which can be carried by aircraft to the site of the fire.

Another object of this invention is to provide a fire control composition which is capable of substantially preventing water run-off so as to keep water in the environs of the fire.

SUMMARY OF THE INVENTION

A composition has been found which can be applied to a forest or a brush fire and will act in concert with water to substantially retard and extinguish the fire in order to prevent the fire from spreading. The compositions of this invention contain surfactants, solvents, foam stabilizers and salts and water. When a composition of the present invention is diluted at or above 0.1% by volume in water and aerated through aerial drop or through a nozzle, it provides a foam which is an effective fire extinguishing agent. The compositions of this invention create and maintain a moist ambient atmosphere which substantially prevents the rekindling of fire.

DETAILED DESCRIPTION OF PREFERRED EMBODIMENTS

Preferably, the compositions of this invention contain the following components:

A. About 1% to about 80% by weight of one or more hydrocarbon surfactants;

B. About 0.1% to about 6% by weight of one or more foam stabilizers;

C. About 0% to about 30% by weight of one or more solvents: and

D. About 1% to about 98.9% by weight of water.

The components act to form a stable foam substantially instantly upon exposure to and/or mixture with air.

Preferably, the hydrocarbon surfactants of this invention can be selected from the group consisting of anionic, amphoteric and nonionic surfactants. Preferably, anionic surfactants are used. More preferably, salt derivatives of linear alcohols of the following formula (I) are employed:

$$[R(OCH_2CH_2)_nX]_aM_b \quad (I)$$

wherein R is an alkyl group having from eight to eighteen carbon atoms, n is an integer from 0 to 10, X is selected from the group of $SO_3^{2-}$, $SO_4^{2-}$, $CO_3^{2-}$; $PO_4^{3-}$; $M^-$ is an alkali metal, alkaline earth metal, ammonium or amine derivatives, and wherein a is the valence of M and b is the valence of $[R(OCH_2CH_2)_nX]$ preferably $Mg^{++}$, $Ca^{++}$, $Na^+$ or $NH_4^+$. One or more surfactants may be used in the composition of this invention. Preferably two surfactants may be used in the ratio of between about 1:1 to about 4:1. More preferably, two surfactants may be used in the ratio of about 1:1. Two surfactants which are preferably used are $C_{10}H_{21}(OCH_2CH_2)_{2-3}SO_4^-NH_4^+$ and $C_{14}H_{29}(OCH_2CH_2)_3SO_4^-NA^+$.

The foam stabilizer component of the compositions of this invention are either preferably compounds having the structure of formula (II):

$$R(OCH_2CH_2)_xOH \quad (II)$$

wherein R is an alkyl group having from 8 to 18 carbon atoms and x is an integer from 0 to 10; or alkanolamides having the structure of formula (III):

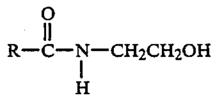

(III)

wherein R is an alkyl group having from 8 to 18 carbon atoms. Component (B) can also be a polysaccharide gum or a synthetic polymer which can serve to decrease the rate of drainage once the composition reaches the ground. One or more types of foam stabilizer may be used in the compositions of this invention.

Component (C) of the compositions of this invention may be solvents which serve to prevent freezing of the composition, to stabilize the foam, to modify viscosity of the composition to assure proper mixing, dispension and proportioning of the foam. Component (C) may also act as a foam booster. Preferably, solvents which may be used in the compositions of this invention include polyhydric alcohol ethers and low molecular weight alcohols. More preferably, solvents may vary selected from the group of ethylene glycol monoalkyl ethers, diethylene glycol monoalkyl ethers, diethylene glycol monoalkyl ethers, propylene glycol monoalkyl ethers, triethylene glycol monoalkyl ethers and 1-butoxy ethoxy-2-propanol. Most preferable are 1-butoxyethanol-2-propanol and diethylene monobutyl ether.

Additional components known to those of skill in the art may be added to the compositions of this invention to buffer the compositions or to inhibit the corrosive effect of the compositions when stored. Examples of corrosion inhibitors are tolyltriazole, potassium chromate and the like. Chelating agents known to those of skill in the art may also be added.

The compositions of this invention are highly biodegradable so as to be substantially non-toxic to the environment.

One preferable composition contains 30% by weight $C_{10}H_{21}(OCH_2CH_2)_{2-3}SO_4^-NH_4^+$, 30% by weight of $C_{14}H_{29}(OCH_2CH_2)_3SO_4^-Na^+$, 5% by weight $C_{12}H_{25}OH$ (lauryl alcohol), 18% diethylene glycol monobutyl ether, 0.5% corrosion inhibitor (tolyltriazole or potassium chromate) and 16.5% water.

Some exemplary compositions of ths invention are set forth in Examples 1 and 2 below. Of course, the Examples below merely set forth some of the embodiments of this invention and serve merely to illustrate and not to limit the compositions of this invention.

The compositions of this invention may be applied aerially, from above the site of the fire, or through a nozzle which pressurizes the composition so as to form foam.

The compositions of this invention are unique because they are able to form foam through an aerial drop. Such foam application extends the area of coverage, provides vapor suppression, isolates the air from the fire so as to prevent the action of air, as a fuel for the conflagration. Further, the compositions of this invention provide a slow solution drainage, thus substantially preventing the run-off of the water/fire retardant solution from the immediate environment of the fire. This provides increased humidity, cooling and solution penetration of the forest floor and canopy through wetting. Thus, evaporation is suppressed and a wetter environment is maintained so as to substantially prevent the fire from starting again or spreading to the area which has been sprayed.

The compositions of this invention may be mixed with water or another inert carrier and dropped from the air. When the mixture of the fire retardant compositions of this invention are dropped from a bucket slung under a helicopter or a fixed wing aircraft, the load should be released between 20 to 40 meters above the forest canopy. If attempting to provide protection of structural property, heights of 70 to 90 meters will allow more of the solution to become expanded foam and cover a larger ground area.

Delivery speeds with a helicopter can vary. In bucketing operations, the fire retardant compositions of this invention may be dumped from a hovering position or from a vehicle having a speed up to 30 knots. Helicopters equipped with a belly tank can dump the compositions up to the maximum speed of the helicopter.

For fixed wing aircraft application, speeds can vary between 90 and 180 knots. When dropped under these conditions, a foam cloud is formed almost instantaneously. The velocity of this cloud diminishes very rapidly, compared to straight water or other mixtures. The foam cloud impacts softly on the cover, causing little damage and envelops the cover, from crown to ground in a layer of foam. Drop patterns may vary with the type of craft and drop mechanism.

Another advantage of the method of this invention is that the compositions, when dropped from a plane or helicopter, from a brilliant white form cloud, which leaves a visible pattern on the trees, thereby providing a marker for subsequent drops.

The foam enveloping the cover permits the water to drain slowly. The draining water from the foam incorporates wetting and extinguishing properties to ensure deep penetration of tree bark, trunk, duff and porous substrates.

The compositions and methods of this invention may be used to fight ground fires as well as forest fires. In ground fire fighting operations, the compositions of this invention may be used with forest fire fighting nozzles, known to those of ordinary skill in the art, hoses, pumps and water tanks of any design. First, the tanks or other equipment is filled with water. Then, the compositions of this inventions may be added to the water or inducted into the water stream by using inline concentrate eductors.

Preferably, for ground fire fighting applications, the compositions of this invention are used at about 0.1% to 1% by volume concentration. However, for both ground and aerial fire fighting, the composition may be mixed with an inert carrier such as sea water or fresh water at a concentration of from about 0.1% about 99.9% by volume. For aerial fire fighting, the concentration is preferably from about 0.1 to about 1.0% by volume concentration.

The compositions of this invention should be used initially to saturate the fringe of the fire area, unless the fire is small, in which case the solution should be cropped earestly onto the visual fire or the smoke emitting through the canopy. On sloping ground or steep mountain sides, the solutions of this invention should be applied from the high side taking advantage of the natural terrain to allow the solution to flow into the fire area. When dropping from fixed wing aircraft, the solution will expand in volume by a ratio of approximately 13:1. The foam will decelerate and drift into a longer and wider pattern than water or typical retardants. Approximately 40% of the payload will hang up in the canopy, depending on its density. The remainder will cascade down through the foliage. The load trapped in the canopy will increase the humidity and continue to weep onto the fire area, deeply penetrating all fibre material. Once everything becomes saturated the interaction of the solution extinguishes the fire.

The compositions of this invention are at least three times as effective as water in extinguishing forest fires. The compositions of this invention may used with any kind of water, fresh or brackish or sea water.

The shelf-life of the compositions of this invention is believed to be approximately twenty to twenty-five years, if stored under normal warehouse conditions. This enables it to be rapidly available prior to the forest fire season and usable the following season without substantial deterioration of performance.

The surfactants present in the compositions of this invention decrease the surface tension of the water applied to the forest fire, thereby providing better penetration of the water itself as well as any rain which may fall in the area.

EXAMPLE 1

A composition according to this invention is made by combining 20% by weight of $C_{10}H_{21}(OCH_2CH_2)_{2-3}SO_4^-NA^+$, 20% by weight of $C_{14}H_{29}(OCH_2CH_2)_3SO_4^-NH_4^+$, 5% by weight of $C_{12}H_{25}OH$, 20% by weight of diethylene glycol monobutyl ether, 0.5% of corrosion inhibitors and 34.5% by weight of water.

EXAMPLE 2

A composition of this invention is made by mixing 20% by weight of $C_{12}H_{25}SO_4^-NH_4^+$, 3% by weight of $C_{12}H_{25}OH$, 3% by weight alkanolamide, 30% by weight of ethylene glycol monobutyl ether, 10% protein (hydrolysate polymer) and 34% water.

EXAMPLE 3

A composition of this invention containing 30% by weight of $C_{10}H_{21}(OCH_2CH_2)_{2-3}SO_3^-NH_4^+$, 30% by weight $C_{14}H_{29}(OCH_2CH_2)_3SO_3^-NA^+$, 5% by weight of $C_{12}H_{25}OH$ (lauryl alcohol), 18% by weight of diethylene glycol monobutyl ether, 0.5% by weight of tolyltriazole and 16.5% by weight of water was placed in a tank. The solution was placed in an injection system, which was installed on a Canadair CL-215 Aircraft 40 owned and operated by Security Civile, Marignane, France. The injection system was installed and preset to induct the composition at 0.85%. The aircraft was directed to attack a small fire near Cannes, by the time the aircraft arrived the small fire had turned into a major fire involving camp sites and personal homes. They dropped twelve loads of solution. Observers could readily spot the area of contact, as the ground was white and the fire was totally extinguished. The aircraft was operated at a speed of approximately 90 knots, at an altitude of 25 to 50 meters, preferably 30 meters above the forest canopy.

The forest was comprised of deciduous growth intermixed with bushes which grew approximately one meter high and in great density. Another type of bush grew two to three meters high. Up through these two growths, parasol pines ormaritime pines grew to a height of 25 to 30 meters. Water had had very little effect on the fire unless applied by several water bombers simultaneously. When fire retardants premixed with water were dropped the foliage was so dense that the retardant became trapped in the upper growth and could not penetrate the thick foliage.

EXAMPLE 4

On a small fire in Cannes, France, a series of drops were made from a Pelican helicopter. The same compositions were used as set forth in Example 3. The compositions were also applied in the manner set forth in Example 3. However, because of the density of the foliage, the induction rate of the composition was changed to 0.6% or 28 liters of composition per drop. At this induction rate, the penetration of the canopy was successful and the fire was extinguished.

EXAMPLE 5

A fire-fighting team traveled to Valencia, Spain. A fire occurred north of Valencia high up in the hills and was burning in a moderate to light stand of pines. A drop was made containing liquid concentrate of the composition described in Example 3 in the same manner as that described in Example 3. A first drop with foam was made at about 300 meters and consequently the foam drifted with the wind and missed the fire completely. The plane was scooping from the sea and the turn-around time was approximately 35 minutes. The next three drops were made at a lower height and extinguished 95% of the fire.

What is claimed is:

1. A composition for retarding and extinguishing a forest fire comprising from about 1% to about 80% by weight of one or more hydrocarbon surfactants, from about 0.1% to about 6% by weight of one or more foam stabilizers, from 0% to about 30% by weight of one or more solvents and about 1% to about 98.9% by weight of water wherein said surfactant composition comprises two anionic surfactants of the formula: $C_{10}H_{21}(OCH_2CH_2)_{2-3}SO_4M$ and $C_{14}H_{29}(OCH_2CH_2)_3SO_4M$ in the ratio of from about 1:1 to about 4:1, wherein M is $NH_4$ or Na.

2. A composition according to claim 1 wherein one of said anionic surfactants is $C_{10}H_{21}(OCH_2CH_2)_{2-3}SO_4^-Na^+$.

3. A composition according to claim 1 wherein one said anionic surfactants is $C_{14}H_{29}(OCH_2CH_2)_3SO_4^-NH_4^+$.

4. A composition according to claim 1 wherein the foam stabilizer component has the formula:

$$R(OCH_2CH_2)_xOH$$

wherein R is an alkyl group having from 8 to 18 carbon atoms and X is an integer from 0 to 10.

5. A composition according to claim 1 wherein said foam stabilizer is an alkanolamide having the formula:

$$R\overset{O}{\overset{\|}{C}}NHCH_2CH_2OH$$

wherein R is an alkyl group having from 8 to 18 carbon atoms.

6. A composition according to claim 4 wherein the foam stabilizer is $C_{12}H_{25}OH$.

7. A composition according to claim 1 wherein the solvent is a low molecular weight alcohol or a polyhydric alcohol ether.

8. A composition according to claim 7 wherein said solvent is selected from the group consisting of ethylene glycol monoalkyl ethers, diethylene glycol monoalkyl ethers, propylene glycol monoalkyl ethers, triethylene glycol monoalkyl ethers and 1-butoxy ethoxy-2-propanol.

9. A composition according to claim 8 wherein said solvent is 1-butoxy-ethoxy-2-propanol or diethylene monobutyl ether.

10. A composition according to claim 1 comprising 30% by weight $C_{10}H_{21}(OCH_2CH_2)_{2-3}SO_4^-NH_4^+$, 30% by weight $C_{14}H_{29}(OCH_2CH_2)_3SO_4NH_4^+$, 5% by weight $C_{12}H_{25}OH$, 18% diethylene monobutyl ether, 0.5% by weight corrosion inhibitor chosen from the group consisting of tolytriazole and potassium chromate and 16.5% by weight water.

11. A composition for extinguishing fires wherein said composition comprises between about 0.1% and about 99.9% of the composition of claim 1 and an inert carrier.

12. A composition according to claim 15 wherein said composition comprises from about 0.1% and 1.0% of the composition of claim 1.

13. A method of extinguishing forest and ground fires comprising dropping from the air a composition according to claim 2.

14. A method according to claim 13 wherein said composition is dropped from a stationary airborne vehicle.

15. A composition according to claim 13 wherein said composition is dropped from an airborne vehicle moving at a rate from 0 to 18 knots.

16. A method according to claim 13 wherein said composition is dropped from a height from about 20 to about 90 meters above the forest canopy.

* * * * *

UNITED STATES PATENT AND TRADEMARK OFFICE

CERTIFICATE OF CORRECTION

PATENT NO. : 4,770,794

DATED : September 13, 1988

INVENTOR(S) : Edward Cundasawmy et al.

It is certified that error appears in the above-identified patent and that said Letters Patent is hereby corrected as shown below:

IN THE SPECIFICATION:

Column 2, line 37: delete "M-" and insert therefor --M--.

line 47: delete "$C_{14}H_{29}$ $(OCH_2CH_2)_3SO_4^{-}NA^{+}$" and insert therefor --$C_{14}H_{29}(OCH_2CH_2)_3$ $SO_4^{-}Na^{+}$--.

Column 3, line 3: delete "dispension" and insert therefor --dispensing--.

Column 4, line 45: delete "cropped earestly" and insert therefor --dropped directly--.

Column 5, line 13: delete "$NA^{+}$" and insert therefor --$Na^{+}$--.

line 28: delete "$NA^{+}$" and insert therefor --$Na^{+}$--.

line 51: insert space between "or" and "maritime".

UNITED STATES PATENT AND TRADEMARK OFFICE

CERTIFICATE OF CORRECTION

PATENT NO. : 4,770,794

DATED : September 13, 1988

INVENTOR(S) : Edward Cundasawmy et al.

It is certified that error appears in the above-identified patent and that said Letters Patent is hereby corrected as shown below:

IN THE CLAIMS:

Claim 15, line 3: delete "18" and insert therefor --180--.

Signed and Sealed this

Twenty-first Day of February, 1989

*Attest:*

DONALD J. QUIGG

*Attesting Officer*

*Commissioner of Patents and Trademarks*